United States Patent
Kiss et al.

(10) Patent No.: US 10,012,593 B2
(45) Date of Patent: Jul. 3, 2018

(54) MICRO PHOTOLUMINESCENCE IMAGING

(71) Applicant: Semilab SDI LLC, Tampa, FL (US)

(72) Inventors: Zoltan Tamas Kiss, Budapest (HU); Laszlo Dudas, Pécel (HU); Zsolt Kovacs, Budapest (HU); Imre Lajtos, Budapest (HU); Gyorgy Nadudvari, Pilisszentivan (HU); Nicolas Laurent, Singapore (SG); Lubomir L. Jastrzebski, Clearwater, FL (US)

(73) Assignee: SEMILAB Semiconductor Physics Laboratory Co., Ltd., Budapest (HU)

( * ) Notice: Subject to any disclaimer, the term of this patent is extended or adjusted under 35 U.S.C. 154(b) by 61 days.

(21) Appl. No.: 14/703,692

(22) Filed: May 4, 2015

(65) Prior Publication Data
US 2016/0328840 A1   Nov. 10, 2016

(51) Int. Cl.
   *G01N 21/64* (2006.01)
   *H04N 5/374* (2011.01)
   *H04N 5/367* (2011.01)

(52) U.S. Cl.
   CPC ......... *G01N 21/6489* (2013.01); *H04N 5/367* (2013.01); *H04N 5/374* (2013.01); *G01N 2021/6423* (2013.01)

(58) Field of Classification Search
   CPC .................................................. G06T 7/0008
   USPC ...................................................... 356/237.5
   See application file for complete search history.

(56) References Cited

U.S. PATENT DOCUMENTS

| | | | |
|---|---|---|---|
| 4,927,778 A | 5/1990 | Abbas | |
| 5,885,843 A | 3/1999 | Ayers | |
| RE38,307 E | 11/2003 | Gustafsson | |
| 7,446,321 B2 | 11/2008 | Laurent | |
| 7,504,642 B2 | 3/2009 | Hummel | |
| 8,064,054 B2 | 11/2011 | Trupke et al. | |
| 2002/0030753 A1* | 3/2002 | Kramer | H04N 5/367 348/308 |
| 2003/0024269 A1* | 2/2003 | Shepard | C03B 27/00 65/29.18 |
| 2003/0089899 A1 | 5/2003 | Lieber | |

(Continued)

FOREIGN PATENT DOCUMENTS

| CN | 102736009 | 10/2012 |
|---|---|---|
| CN | 103808727 | 5/2014 |

(Continued)

OTHER PUBLICATIONS

Chinese Office Action in Chinese Application No. 201410399797.7, dated Oct. 9, 2016, 7 pages.

*Primary Examiner* — Tarifur Chowdhury
*Assistant Examiner* — Omar Nixon
(74) *Attorney, Agent, or Firm* — Fish & Richardson P.C.

(57) ABSTRACT

In an example implementation, a method includes illuminating a wafer with excitation light having a wavelength and intensity sufficient to induce photoluminescence in the wafer. The method also includes detecting photoluminescence emitted from a portion of the wafer in response to the illumination, and detecting excitation light reflected from the portion of the wafer. The method also includes comparing the photoluminescence emitted from the portion of the wafer and the excitation light reflected from the portion of the wafer, and identifying one or more defects in the wafer based on the comparison.

43 Claims, 2 Drawing Sheets

(56) References Cited

U.S. PATENT DOCUMENTS

| | | | |
|---|---|---|---|
| 2004/0092042 A1* | 5/2004 | Higgs | G01N 21/55 438/14 |
| 2007/0007466 A1 | 1/2007 | Laurent | |
| 2007/0008518 A1 | 1/2007 | Hummel | |
| 2007/0008526 A1 | 1/2007 | Buczkowski | |
| 2008/0213926 A1 | 9/2008 | Tajima et al. | |
| 2011/0025839 A1* | 2/2011 | Trupke | G01N 21/6489 348/87 |
| 2011/0234790 A1 | 9/2011 | True | |
| 2012/0111396 A1* | 5/2012 | Saylor | H01L 31/068 136/255 |
| 2012/0142125 A1 | 6/2012 | Trupke et al. | |
| 2012/0248335 A1 | 10/2012 | Kim et al. | |
| 2013/0016346 A1* | 1/2013 | Romanovsky | G01N 21/9501 356/237.5 |
| 2013/0043405 A1 | 2/2013 | Maxwell et al. | |
| 2013/0169283 A1 | 7/2013 | Lagowski et al. | |
| 2014/0234994 A1* | 8/2014 | Abe | G01N 21/6489 438/16 |
| 2014/0273313 A1 | 9/2014 | Kumar et al. | |
| 2014/0353523 A1* | 12/2014 | Voronov | G01N 21/6489 250/459.1 |
| 2015/0008952 A1 | 1/2015 | Lagowski et al. | |
| 2015/0146193 A1* | 5/2015 | Buczkowski | G01N 21/6489 356/72 |
| 2015/0168303 A1 | 6/2015 | Trupke et al. | |
| 2015/0212011 A1* | 7/2015 | Lombez | G01N 21/9501 702/182 |
| 2016/0327485 A1 | 11/2016 | Kiss et al. | |

FOREIGN PATENT DOCUMENTS

| | | | |
|---|---|---|---|
| TW | 201043943 | 12/2010 | |
| TW | 201727215 | 8/2017 | |
| WO | WO 2012027788 | 3/2012 | |
| WO | WO 2014020046 A1 * | 2/2014 | G01N 21/9501 |

* cited by examiner

MICRO PHOTOLUMINESCENCE IMAGING

TECHNICAL FIELD

This disclosure relates to identifying defects in integrated circuit devices, such as complementary metal-oxide semiconductor imaging sensors.

BACKGROUND

A complementary metal-oxide semiconductor (CMOS) imaging sensor (CIS) is an integrated circuit (IC) device used to convert a light intensity pattern into electric digital signals. In some cases, a CIS is a two dimensional array of photodiodes with accompanying CMOS logic for signal processing. Each individual photodiode with processing CMOS logic is referred to a pixel. In some cases, a CIS has 1,000,000 or more pixels.

A CIS is commonly fabricated on n/n++ or p/p++ wafers. As an example, in some cases, thin lightly doped n-type or p-type epitaxial layers (e.g., 3-5 μm layers each having a dopant concentration of $1 \times 10^{14}$ to $1 \times 10^{15}$ cm$^{-3}$) are grown on a highly doped n++ or p++ substrate (e.g., a substrate having a dopant concentration of $1 \times 10^{18}$ to $1 \times 10^{20}$ cm$^{-3}$). A CIS is formed on the epitaxial layers, a region often referred to as the device active area. Performance of the CIS is influenced, at least in part, by properties of this active area.

The highly doped substrates (often referred to as handles) provide mechanical support for the active area during the CIS fabrication process. In some cases, the substrate also reduces the occurrence of cross-talk in a CIS. For example, the substrate can reduce the cross-talk that results when minority carriers generated underneath one pixel in response to red light reach adjacent pixels of the CIS.

A CIS can be arranged according to a variety of different configurations. For example, a CIS can be arranged as a front side illuminated (FSI) CIS, or as a back side illuminated (BSI) CIS. Here, the "front" side refers to the side of the wafer on which the IC pixel structures are fabricated. In some cases, to make a BSI CIS, a CIS wafer first undergoes CIS processing on its front side. The CIS wafer is then bonded along its front side to a wafer carrier, and its backside is thinned (e.g., by a few μm) until all of its n++ or p++ substrate is removed. The surface of the CIS wafer is then passivated and covered with an antireflection coating, and color filters are fabricated on its back side. During use, a light image is projected on the back side of the CIS wafer, and the CIS converts the light image into electric digital signals.

Light from an image projected on a CIS having photon energy larger than the silicon band gap is primarily absorbed in the CIS active area. This absorption generates electron and hole pairs, resulting in photocurrent. These photo-generated minority carriers are then collected by a p-n junction at this location. The number of photo-generated minority carriers is proportional to the number of photons that are absorbed in the CIS active area, and varies according to the intensity of light. Thus, the intensity of light incident upon the CIS active area can be deduced based on the magnitude of the generated photocurrent. In practice, it is often desirable for each of the pixels of a CIS to generate identical or substantially similar photocurrent in response to uniform, low level illumination. Otherwise, pixels having lower or higher photocurrent (e.g., "defective" pixels) might result in bright or dark spots in the resulting image.

In some cases, localized crystallographic defects and heavy metal contaminations could increase or decrease photocurrent from a given pixel, resulting in an image having bright spots or dark spots at low illumination levels. When present in a space charge region of the p-n junctions, these defects act as generation centers for minority carriers. This results in an increase in the dark current of these pixels, and if the defect is sufficiently severe, will result in white or bright spots in the resulting image. When present outside of the space charge region of p-n junctions, these defects act as recombination centers for minority carriers. This results in a decrease in the amount of photocurrent collected by the junctions, and if the defect is sufficiently severe, will result in as dark spots in the resulting image at low illumination levels.

Localized crystallographic defects or heavy metal contaminations can potentially be introduced at any step during the fabrication process of a CIS. Thus, to improve and control the fabrication process of a CIS, it is important to quickly identify processing steps that are introducing these defects.

SUMMARY

Systems and techniques for identifying defects in integrated circuit devices are described herein.

In general, in an aspect, a method includes illuminating a wafer with excitation light having a wavelength and intensity sufficient to induce photoluminescence in the wafer. The method also includes detecting photoluminescence emitted from a portion of the wafer in response to the illumination, and detecting excitation light reflected from the portion of the wafer. The method also includes comparing the photoluminescence emitted from the portion of the wafer and the excitation light reflected from the portion of the wafer, and identifying one or more defects in the wafer based on the comparison.

In general, in another aspect, a system includes an illumination module configured to illuminate a wafer with excitation light having a wavelength and intensity sufficient to induce photoluminescence in the wafer, a first detection module configured to detect photoluminescence emitted from a portion of the wafer in response to the illumination, a second detection module configured to detect excitation light reflected from the portion of the wafer, and processing module. The processing module is configured to compare the photoluminescence emitted from the portion of the wafer and the excitation light reflected from the portion of the wafer, and identify one or more defects in the wafer based on the comparison.

Implementations of these aspects may include or more of the following features.

In some implementations, the wafer can include a complementary metal-oxide semiconductor (CMOS) imaging sensor. The portion of the wafer can include one or more pixels of the CMOS imaging sensor. Identifying one or more defects in the wafer can include identifying one or more defective pixels of the CMOS imaging sensor. Detecting photoluminescence emitted from the portion of the wafer can include resolving photoluminescence emitted from the portion of the wafer at a spatial resolution of 1 μm×1 μm or smaller. Detecting excitation light reflected from the portion of the wafer can include resolving excitation light reflected from the portion of the wafer at a spatial resolution of 1 μm×1 μm or smaller. Identifying one or more defects in the wafer can include identifying one or more defects having a dimension of 1 μm or smaller. The portion of the wafer can correspond to an active area of the CMOS imaging sensor.

In some implementations, the method can further include forming a photoluminescence intensity map of the portion of the wafer based on the photoluminescence emitted from the portion of the wafer, and forming a reflection intensity map of the portion of the wafer based on the excitation light reflected from the portion of the wafer. In some cases, the processing module can be further configured to form a photoluminescence intensity map of the portion of the wafer based on the photoluminescence emitted from the portion of the wafer, and form a reflection intensity map of the portion of the wafer based on the excitation light reflected from the portion of the wafer. Comparing the detected photoluminescence from the portion of the wafer and the detected reflected excitation light from the region of the wafer can include determining that the photoluminescence intensity map includes a first variation in intensity at a first location of the wafer; upon determining that the photoluminescence intensity map includes the first variation in intensity at the first location of the wafer, determining whether the reflection intensity map includes a second variation in intensity at the first location of the wafer; and upon determining that the reflection intensity map does not include a second variation in intensity at the first location of the wafer, determining that a defect is present at the first location of the wafer. Comparing the detected photoluminescence from the portion of the wafer and the detected reflected excitation light from the region of the wafer can further include, upon determining that the reflection intensity map includes the second variation in intensity at the first location of the wafer, determining that a defect is not present at the first location of the wafer.

In some implementations, the method can further include detecting photoluminescence emitted from a second portion of the wafer, where the second portion of the wafer is larger than the first portion of the wafer. The method can also include forming a photoluminescence intensity map of the second portion of the wafer based on the photoluminescence emitted from the second portion of the wafer. The method can also include determining the presence of one or more curved regions of contrast in the photoluminescence intensity map, and upon determining the presence of one or more curved regions of contrast in the photoluminescence intensity map, adjusting a property of the excitation light. In some cases, the system can further include a third detection module configured to detect photoluminescence emitted from a second portion of the wafer, where the second portion of the wafer is larger than the first portion of the wafer. The processing module can be further configured to form a photoluminescence intensity map of the second portion of the wafer based on the photoluminescence emitted from the second portion of the wafer, determine the presence of one or more curved regions of contrast in the photoluminescence intensity map, and upon determining the presence of one or more curved regions of contrast in the photoluminescence intensity map, adjust a property of the excitation light. Adjusting the property of the excitation light can include adjusting a wavelength of the excitation light to increase the photoluminescence emitted from the second portion of the wafer. Adjusting the property of the excitation light can include adjusting an intensity of the excitation light.

In some implementations, illuminating the wafer with excitation light can include illuminating the wafer with excitation light such that Auger recombination does not substantially occur in the portion of the wafer.

In some implementations, the excitation light can have a wavelength in a range from 200 nm to 1100 nm.

In some implementations, the photoluminescence can have as a wavelength in a range from 200 nm to 1100 nm.

Among other advantages, embodiments may be used to identify localized defects in a CIS device during the manufacturing process (e.g., during or between intermediate steps of the manufacturing process of the CIS device) and/or after the completion of the manufacturing process (e.g., as a part of a post-manufacturing inspection). In some cases, embodiments can be used to identify defects associated with a single pixel of the CIS device, such that one or more individual defective pixels can be identified in a CIS device. In some cases, embodiments can be used to reduce the number of positives that might otherwise result during the defect detection process due to the presence of particulate matter on a CIS device.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Defects in a CIS device can be identified by inducing photoluminescence in the active region of the CIS device, and examining the photoluminescence for localized variations in intensity.

In general, photoluminescence can be induced in a silicon wafer with light having photon energy larger than the energy gap of silicon (e.g., more than 1.1 eV). As this light is absorbed in the silicon, electron-hole pairs are generated in the silicon. Some of these photo-generated carriers will recombine through radiative recombination and release photons of light, a phenomenon known as photoluminescence.

As the intensity of photoluminescence varies depending on the composition of the wafer, localized variation in the composition of the wafer (e.g., resulting from material defects or contaminations) will result in localized variation in the induced photoluminescence. Thus, defects in a CIS device can be identified, at least in part, by illuminating a CIS device with excitation light sufficient to induce photoluminescence, and examining the photoluminescence for localized variations in intensity.

Figure 1:
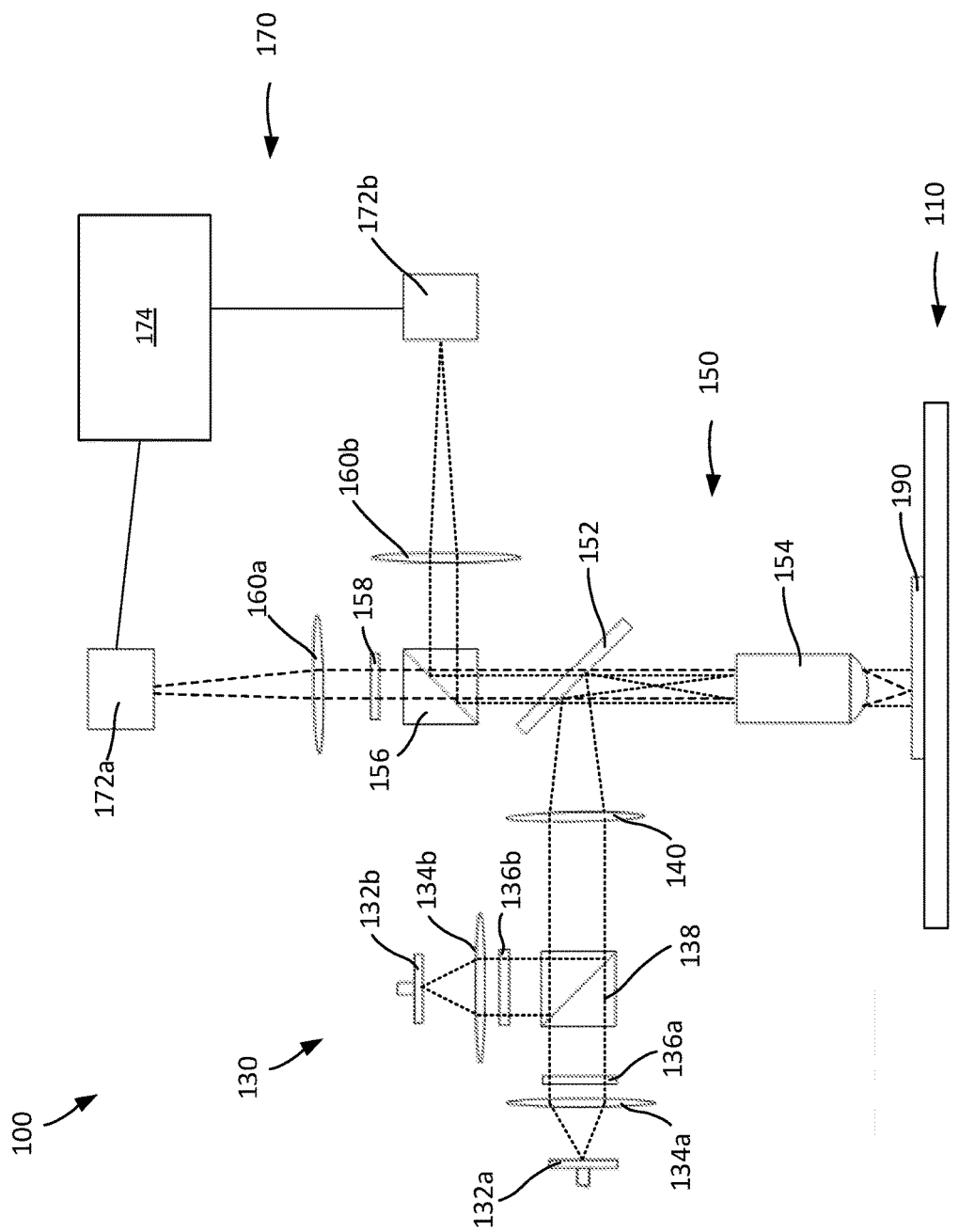
FIG. 1 shows an example system for detecting defects in a CIS sample.

An example system 100 for identifying defects in a CIS is shown in FIG. 1. The system 100 includes a stage assembly 110, an illumination assembly 130, an optical assembly 150, and an imaging assembly 170. In an example usage of system 100, a CIS sample 190 is placed on the stage assembly 110 and is positioned for examination. The illumination assembly 130 generates excitation light suitable for inducing photoluminescence in the CIS sample 190. The optical assembly 150 directs the excitation light generated by the illumination assembly 130 onto the CIS sample 190, thereby inducing photoluminescence in the CIS sample 190 and/or causing excitation light to be reflected by the CIS sample 190. The optical assembly directs the photoluminescence generated by the CIS sample 190 and/or light reflected by the CIS sample 190 towards the imaging assembly 170. The imaging assembly 170 detects the photoluminescence and reflected excitation light, and identifies defects in the CIS sample based 190 on the detected light.

The stage assembly 110 supports the CIS sample 190 during examination by the system 100. In some cases, the stage assembly 110 can move along one or more axes, such that the CIS sample 190 can be moved related to the illumination assembly 130, optical assembly 150, and/or the imaging assembly 170. For example, in some cases, the CIS can move along the x, y, and z axes of a Cartesian coordinate system in order to move the CIS sample 190 along any of three dimensions related to the other components of the system 100.

The illumination assembly 130 generates excitation light that, when incident upon the CIS sample 190, induces photoluminescence in the CIS sample 190. The illumination assembly 130 includes light sources 132a-b, collimating lenses 134a-b, filters 136a-b, dichroic beam splitter 138, and focusing lens 140.

Light sources 132a-b generate light having particular properties suitable for inducing photoluminescence in the CIS sample 190. In some cases, the light sources 102a-b are laser light sources that generate light having a particular wavelength and intensity. In some cases, the light sources 132a-b each generate light having a different wavelengths, such that the illumination assembly 130 can provide different types of light. For example, the light source 132a can generate light having a first wavelength (e.g., 532 nm), and the light source 132b can generate light having a second wavelength (e.g., 880 nm). The light sources 132a-b can be operated independently from one another, such that light at each of the different wavelengths can be individually or simultaneously generated. Light sources 132a-b include any component capable to generating light at a specified wavelength. For example, in some cases, the light sources 132a-b can include one or more lasers or light emitting diodes (LEDs).

In some cases, the light sources 132a-b each generate light having a different wavelengths, such that the illumination assembly 130 can provide different types of light. For example, the light source 132a can generate light having a first wavelength (e.g., 532 nm), and the light source 132b can generate light having a second, different wavelength (e.g., 880 nm). As another example, either or both of the light sources 132a-b can generate light having a wavelength less than 532 nm (e.g., 300 nm, 350 nm, 400 nm, 450 nm, 500 nm, or any intermediate wavelength thereof). As yet another example, either or both of the light sources 132a-b can generate light having a wavelength between 200 nm and 1100 nm (e.g., 200 nm, 300 nm, 400 nm, 500 nm, 600 nm, 700 nm, 800 nm, 900 nm, 1000 nm, 1100 nm, or any intermediate wavelength thereof). Although example wavelengths are described above, these are merely illustrative examples. In practice, the light sources 132a-b can each generate light having any other wavelengths, depending on the implementation.

The light generated by the light sources 132a-b can also vary in intensity, depending on the implementation. As an example, in some cases, the light sources 132a-b can each generate light having a power between 0.02 W and 20 W. In some cases, the intensity of light generated by the light sources 132a-b can also be adjusted during use of the system 100. For example, in some cases, the light generated by the light sources 132a-b can be adjusted between 0.02 W and 20 W during operation of the system 100. As another example, in some cases, the light generated by the light sources 132a-b can be adjusted during operation of the system 100 such that they generate light having a power less than 0.02 W (e.g., 0.015 W, 0.010 W, or 0.005 W). Although example intensities are described above, these are merely illustrative examples. In practice, the light sources 132a-b can each generate light having other intensities, depending on the implementation.

Excitation light generated by the light sources 132a-b are directed towards collimating lenses 134a-b, respectively. The collimating lenses 134a-b narrows the beam of passing light, such that the light exiting the collimating lenses 134a-b are aligned along the optical axes of collimating lenses 134a-b, respectively.

The collimated excitation light from collimating lenses 134a-b are directed into filters 136a-b, respectively. The filters 136a-b filter the passing light, such that only light having particular wavelengths or range of wavelengths are substantially transmitted through the filters 136a-b, respectively. The filters 136a-b can be used to "clean" the light generated by the light sources 132a-b. For example, if the light source 132a generates light having a first wavelength (e.g., 532 nm), the filter 136a can be a band-pass filter that transmits light having a range of wavelengths that includes the first wavelength (e.g., 522 nm to 542 nm), while light having wavelengths outside of this range are not substantially transmitted. As another example, if the light source 132b generates light having a first wavelength (e.g., 880 nm), the filter 136b can be a band-pass filter that transmits light having a range of wavelengths that includes the second wavelength (e.g., 870 nm to 890 nm), while light having wavelengths outside of this range are not substantially transmitted. In some cases, for example in implementations in which the light sources 132a-b include one or more lasers, the filters 136a-b can also include speckle-reducing elements (e.g., a moving diffuser element) in order to reduce the effects of interference effects in the laser beam.

The filtered excitation light from the filters 136a-b are directed into a dichroic beam splitter 138. The dichroic beam splitter 138 reflects light and/or transmits light, depending on the wavelength of light incident upon it. For example, if the light source 132a generates light having a first wavelength (e.g., 532 nm) and the light source 132b generates light having a second wavelength (e.g., 880 nm), the dichroic beam splitter 138 can transmit light having the first wavelength and reflects light having the second wavelength. As a result, although light generated by each of the light sources 132a-b are initially directed in substantially different directions, dichroic beam splitter 138 redirects the light in a substantially similar direction.

The excitation light from the dichroic beam splitter 138 is directed to a focusing lens 140. The focusing lens 140 focuses the light towards the optical assembly 150.

The optical assembly 150 directs the excitation light generated by the illumination assembly 130 towards the CIS sample 190, and directs photoluminescence generated by the CIS sample 190 and/or light reflected by the CIS sample 190 towards the imaging assembly 170. The optical assembly 150 includes dichroic beam splitters 152 and 156, an objective lens 154, a filter 158, and field lenses 160a-b.

The excitation light from the focusing lens 140 is directed to the dichroic beam splitter 152. The dichroic beam splitter 152 reflects light and/or transmits light, depending on the wavelength of light incident upon it. For example, if the light source 130a generates excitation light having a first wavelength (e.g., 532 nm), the light source 130b generates excitation light having a second wavelength (e.g., 880 nm), and photoluminescence induced in the CIS sample 190 has a third wavelength (e.g., 1100 nm), dichroic beam splitter 152 can partially reflect and partially transmit the light at each of these wavelengths. Thus, at least some of the excitation light received from the illumination assembly 130 is redirected by the dichroic beam splitter 152 towards the objective lens 154, at least some of the photoluminescence induced in the CIS sample 190 is transmitted by the dichroic beam splitter 152 towards the imaging assembly 170, and at least some of the excitation light reflected by the CIS sample 190 is also transmitted towards the imaging assembly 170.

The excitation light from the dichroic beam splitter 152 is directed to an objective lens assembly 154. The objective lens assembly 154 directs the excitation light onto the CIS sample 190. In some cases, the objective lens assembly 154 can direct the excitation light onto a particular region of the CIS sample 190 (e.g., a region of the CIS sample 190 that is being examined), such that the intensity of excitation light incident upon that region of the CIS sample 190 is uniform or substantially uniform. This region can be, for example, the entirety of the CIS sample 190 or a portion of the CIS sample 190.

The excitation light incident on the CIS sample 190 can induce photoluminescence in the CIS sample 190. In some cases, the photoluminescence in the CIS sample 190 can have a wavelength between 200 nm and 1100 nm (e.g., 200 nm, 300 nm, 400 nm, 500 nm, 600 nm, 700 nm, 800 nm, 900 nm, 1000 nm, 1100 nm, or any intermediate wavelength thereof).

The objective lens assembly 154 can focus on particular regions of the CIS sample 190 in order to obtain photoluminescence from these regions. In some cases, the objective lens assembly 154 can focus on a region of the CIS sample 190 that includes one or more pixels of the CIS sample 190, and the objective lens assembly 154 can include a lens element having a wide angle and shallow depth of field, such that it resolves photoluminescence from each of the pixels within that region. In some cases, the objective lens assembly have a lens element having a focal length between 0.5 mm and 550 mm, and a depth of field between 1 µm and 400 µm. In some cases, the objective lens assembly 154 can resolve light with sufficient resolution to distinguish photoluminescence from each of the pixels. For example, if the CIS sample 190 includes pixels having dimensions of 1 µm×1 µm along the surface, the objective lens assembly 154 can resolve photoluminescence at a spatial resolution of 1 µm×1 µm or finer.

The excitation light incident on the CIS sample 190 can also result in the reflection of excitation light from the CIS sample 190. The objective lens assembly 154 can also focus on particular regions of the CIS sample 190 in order to obtain excitation light reflected from these regions. In an similar manner as above, in some cases, the objective lens assembly 154 can focus on a region of the CIS sample 190 that includes one or more pixels of the CIS sample 190, and the objective lens assembly 154 can include a lens element having a wide angle and shallow depth of field, such that it resolves excitation light reflected from each of the pixels within that region. In a similar manner as above, some cases, the objective lens assembly 154 can resolve light with sufficient resolution to distinguish excited light reflected from each of the pixels. For example, if the CIS sample 190 includes pixels having dimensions of 1 µm×1 µm along the surface, the objective lens assembly 154 can resolve reflected light at a spatial resolution of 1 µm×1 µm or finer.

In some cases, the objective lens assembly 154 can be refocused in order to resolve light from different regions of the CIS sample 190. For example, in some implementations, the focal depth of objective lens assembly 154 can be varied in order to examine photoluminescence from varying depths from the surface of the CIS sample 190 (e.g., from the back surface of the CIS sample 190 to the front surface of the CIS sample 190).

In some cases, the magnification of the objective lens assembly 154 also can be changed in order to examine particular regions of the CIS sample 190 in greater or lesser detail. In some cases, the magnitude of the objective lens assembly 154 can be changed by moving lens elements of the objective lens assembly 154 relative to one another (e.g., a "zoom" lens), or by otherwise modifying the light path of light through the objective lens assembly 154.

The photoluminescence and reflected excitation light is directed by the objective lens assembly 154 to the dichroic beam splitter 152. As described above, the dichroic beam splitter 152 reflects light and/or transmits light, depending on the wavelength of light incident upon it. For example, if the light source 130a generates excitation light having a first wavelength (e.g., 532 nm), the light source 130b generates excitation light having a second wavelength (e.g., 880 nm), and photoluminescence induced in the CIS sample 190 has a third wavelength (e.g., 1100 nm), dichroic beam splitter 152 can partially reflect and partially transmit the light at each of these wavelengths. Thus, at least some of the photoluminescence and reflected excitation light is transmitted by the dichroic beam splitter 152 towards the imaging assembly 170.

At least a portion of the photoluminescence and reflected excitation light is directed by the dichroic beam splitter 152 to the dichroic beam splitter 156. The dichroic beam splitter 156 also reflects light and/or transmits light, depending on the wavelength of light incident upon it. For example, if the light source 130a generates excitation light having a first wavelength (e.g., 532 nm), the light source 130b generates excitation light having a second wavelength (e.g., 880 nm), and photoluminescence induced in the CIS sample 190 has a third wavelength (e.g., 1100 nm), dichroic beam splitter 156 can reflect excitation light having the first and second wavelengths, and transmit photoluminescence having the third wavelength. As a result, photoluminescence and reflected excitation light are redirected along different optical paths.

Photoluminescence transmitted by the dichroic beam splitter 152 is directed through a filter 158. The filter 158 filters the passing light, such that only light having particular wavelengths or range of wavelengths are substantially transmitted through the filter 158. The filter 158 can be used to "clean" the output of the dichroic beam splitter 152. For example, if photoluminescence from the CIS sample 190 is expected to have a particular wavelength (e.g., 1100 nm), the filter 158 can be a band-pass filter that transmits light having a range of wavelengths that includes the photoluminescence wavelength (e.g., 1000 nm to 1200 nm), while light having wavelengths outside of this range are not substantially transmitted. As another example, in some cases, the filter 158 can be a long-pass filter that attenuates light having relatively shorter wavelengths, while transmitting light having relatively longer wavelengths. This can be helpful, for example, in filtering out reflected excitation light, which in many cases has a shorter wavelength than the photoluminescence from the CIS sample 190.

Photoluminescence and the reflected excitation light are then directed to field lenses 160a-b respectively. The field lenses 160a-b focus the photoluminescence and the reflected excitation light towards the detectors 172a-b, respectively, of the optical assembly 170.

The imaging assembly 170 detects the photoluminescence and reflected excitation light, and identifies defects in the CIS sample based 190 on the detected light. The imaging assembly 170 includes detectors 172*a-b*, and a processing module 174.

The detectors 172*a-b* measure the photoluminescence and the reflected excitation light, respectively, from the dichroic beam splitter 152. In some cases, the detectors 172*a-b* are configured to measure the intensity of light at a sufficiently high spatial resolution to resolve photoluminescence and the reflected excitation light for a single pixel of the CIS sample 190. For example, if the CIS sample 190 includes pixels having dimensions of 1 μm×1 μm along the surface, the detectors 172*a-b* can each resolve photoluminescence at a spatial resolution of 1 μm×1 μm or finer. In some cases, the detectors 172*a-b* can include a single detection element that measures the intensity of light incident upon it, or several such detection elements. For example, in some cases, the detectors 172*a-b* can include a line of detection elements (e.g., a "line" detector), or a two dimensional array of detection elements. In some cases, the detectors 172*a-b* can be include one or more InGasAs line cameras or arrays, or Si line cameras or arrays.

In some cases, the detectors 172*a-b* measure the photoluminescence and the reflected excitation light, respectively, by integrating the intensity of light received over a period of time. This integration time can depend, at least in the part, on the intensity of light that is applied to the CIS sample 190. For example, in some cases, reducing the intensity of light incident on the CIS sample 190 by a factor of two can result in an increase in the integration time by a factor of two. As measurement noise from the detector increases with integration time, in some cases, the intensity of light that is applied to the CIS sample 190 can be adjusted in order to limit the resulting measurement noise of the detectors 172*a-b* to appropriate levels. In some cases, the detectors 172*a-b* can be cooled in order to further reduce measurement noise. For example, in some cases, either or both of the detectors 172*a-b* can be cooled (e.g., by a Peltier cooler) to a particular temperature (e.g., 100 K) in order to reduce the amount of noise in the resulting measurements.

Measurements from the detectors 172*a-b* are transmitted to the processing module 174 for interpretation. In some cases, processing module 174 can generate one or more multiply dimensional maps that represent the intensity of photoluminescence and reflected excitation light for a particular portion of the CIS sample 190. For example, in some cases, the detectors 172*a-b* can include a two dimensional array of detection elements that each measure the intensity of light incident upon that detection element. Using this information, the processing module 174 can generate spatial maps that represent the intensity of photoluminescence and reflected excitation light for at specific locations on the CIS sample 190.

The processing module 174 can also identify defects in the CIS sample 190 based on the measurements from the detectors 172*a-b*. For example, the processing module 174 can identify regions of the CIS sample 190 with a localized variation in photoluminescence (e.g., a spot, blotch, line, curve, or other region having photoluminescence that more intense or less intense than the surrounding regions). The processing module 174 can identify these regions of the CIS sample 190 as having defects. In some cases, the processing module 174 can identify one or more specific pixels of the CIS sample 190 as being defective (e.g., pixels associated with the localized variation in photoluminescence).

In some cases, localized variation in photoluminescence might not be the result of defects in the CIS sample, but rather might be the result of particulate matter on the surface of the CIS sample. As particulate matter can block or otherwise attenuate light, the presence of these particulates can locally affect the intensity of excitation light incident on the CIS sample, and can result in localized variation in photoluminescence. To distinguish between localized variations in photoluminescence as a result of defects in the CIS sample from those as a result of particulate matter, the processing module 174 can determine if regions of the CIS sample 190 identified as having localized variations in photoluminescence also have corresponding localized variations in reflected excitation light.

As an example, if a region has both a localized variation in photoluminescence and a corresponding localized variation in reflected light, the processing module 174 determines that the variation in photoluminescence is the result of particulate matter on the surface of the CIS sample, and not a defect or contamination in the CIS sample. Thus, the processing module 174 can determine that no defect exists in this region.

As another example, if the region has a localized variation in photoluminescence, but does not have a corresponding localized variation in reflected light, the processing module 174 determines that the variation in photoluminescence is not the result of particulate matter on the surface of the CIS sample. Thus, the processing module 174 can determine that a defect exists in this region.

In some implementations, the processing module 174 can be implemented using digital electronic circuitry, or in computer software, firmware, or hardware, or in combinations of one or more of them. For example, in some cases, the processing module 174 can be implemented, at least in part, as one or more computer programs (e.g., one or more modules of computer program instructions, encoded on computer storage medium for execution by, or to control the operation of, a data processing apparatus). A computer storage medium can be, or can be included in, a computer-readable storage device, a computer-readable storage substrate, a random or serial access memory array or device, or a combination of one or more of them. The term "processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

Although an example system 100 is shown and described, this is merely an illustrative example. In practice, the system 100 can have other arrangements, depending on the implementation.

Implementations of the system 100 can be used to identify localized defects in a CIS device during the manufacturing process of the CIS device (e.g., before, during, or after any step during the manufacturing process), and/or after the completion of the manufacturing process. For example, in some cases, implementations of the system 100 can be used to monitor one or more intermediate steps in the manufacturing process of one or more CIS devices, and/or to inspect one or more completed CIS devices.

In some cases, when defects are detected in a CIS device, information regarding the location and nature of the defects can be used to modify the manufacturing process such that fewer and/or less severe defects are introduced into CIS devices in the future. For example, information regarding the detection of defects can be used to identify particular manufacturing equipment or processes that are partially or wholly responsible for the defects. This information can then be used to repair and/or replace that equipment, or to modify the processes in order to improve the manufacturing process. In some cases, information regarding the location and nature of the defects can also be used to identify wafers or portions of wafers that are defective, such that these wafers or portions of wafers can be discarded or otherwise not used in future processes.

Implementations of the system 100 can be used to identify localized defects in a CIS device with a spatial resolution of at least a single pixel of the CIS device. For example, in some cases, a CIS device build with 32 nm technology has pixels of approximately 0.9×0.9 µm; implementations of the system 100 can be used to identify localized defects in this CIS device with a spatial resolution of 0.9×0.9 µm or finer.

In general, the system 100 can generate various different types of excitation light, depending on the application. For instance, in some cases, the system 100 can vary the wavelength of excitation light generated by the illumination module 130 in order to probe different depths under the surface of the CIS sample 190. As an example, in some cases, the illumination module 130 can generate green light (e.g., having a wavelength of approximately 532 or 540 nm) in order to generate minority carriers and photoluminescence close to the surface of the CIS sample 190 (e.g., where 1/(absorption coefficient)=1.5 µm). On the other hand, in some cases, the illumination module 130 can generate near infrared illumination (e.g., having a wavelength of approximately 880 nm) in order to generate minority carriers and photoluminescence further away from the silicon surface. As described above, the illumination module 130 can include multiple light sources, and each light source can be selectively activated in order to product light having a different wavelength. For instance, in the example system 100 shown in FIG. 1, the illumination module 130 can include two light sources, 132a-b, each configured to product light having a different wavelength. The light sources 132a-b can thus be selectively switching on or off in order to probe different depths below the surface of the CIS sample 190. Although two light sources 132a-b are shown, in practice, a system 100 can include any number of light sources, depending on the implementation.

In some cases, the system 100 can vary the intensity of excitation light generated by the illumination module 130. In some cases, the excitation light generated by the illumination module 130 can have an intensity that is sufficiently high to induce photoluminescence in the CIS sample 190, and also sufficiently low to such that Auger recombination does not substantially occur in the illuminated portion of the CIS sample 190.

In general, for a low injection level (e.g., when the minority carrier concentration is less than the majority carrier concentration), the intensity of photoluminescence is proportion to a product of the minority carrier concentration and the majority carrier concentration at a particular location. For example, this can be expressed as:

$$PL = A * C_{minority\ carrier} * C_{majority\ carrier},$$

where PL is the intensity of induced photoluminescence at a particular location (expressed as a number of photons), $C_{minority\ carrier}$ is the minority carrier concentration at that location, $C_{majority\ carrier}$ is the majority carrier concentration at that location, and A is a constant.

The minority carrier concentration $C_{minority\ carrier}$ (referred to as an injection level) is proportional to an effective life time of minority carriers and a generation rate (i.e., the number of photons adsorbed in the silicon normalized to the volume of silicon where minority carriers are present). For example, this can be expressed as:

$$C_{minority\ carrier} = R_{generation} * t_{life,effective},$$

where $R_{generation}$ is the generation rate at the location and $t_{life,effective}$ is the effective life time of minority carriers at the location.

The intensity of induced photoluminescence at a particular location PL is proportional to the intensity of photoluminescence-inducing light absorbed in the silicon at that location (expressed as a number of photons), the effective life time of minority carriers at that location, and the dopant concentration in the silicon at that location. For example, this can be expressed as:

$$PL = A * I_{absorbed} * t_{life,effective} * C_{majority\ carrier},$$

where $I_{absorbed}$ is the intensity of photoluminescence-inducing light absorbed in the silicon at the location (expressed as a number of photons).

The effective life time $t_{life,effective}$ has contributions from various recombination channels, in particular the bulk recombination, the recombination at the interfaces, and the Auger recombination. For example, this can be expressed as:

$$1/t_{life,effective} = 1/t_{recombination,bulk} + 1/t_{recombination,interfaces} + 1/t_{recombination,Auger},$$

where $t_{recombination,bulk}$ is the bulk recombination life time, $t_{recombination,interfaces}$ is the interfaces recombination life time, and $t_{recombination,Auger}$ is the Auger recombination life time.

Defects at interfaces of a pixel (e.g., at the front surface, the back surface, or the walls of the deep trench insulation (DTI) reduces the effective life time $t_{life,effective}$ in a given pixel, and will cause a reduction of photoluminescence intensity from this pixel. For example, this can be expressed as:

$$1/t_{life,interfaces} = 1/t_{recombination,front} + 1/t_{recombination,back} + 1/t_{recombination,DTI},$$

where $t_{recombination,front}$ is the front surface recombination life time, $t_{recombination,back}$ is the back surface recombination life time, and $t_{recombination,DTI}$ is the Deep Trench Isolation (DTI) wall recombination life time.

The interface recombination life time $t_{life,interfaces}$ is inversely proportional to surface (i.e., interface) recombination velocity at this interface and the distance between these interfaces. For example, this can be expressed as:

$$t_{life,interfaces} = \frac{1}{2} * \frac{d_{interfaces}}{v_{recombination,interface}},$$

where $d_{interfaces}$ is the distance between interfaces, and $v_{recombination,interface}$ is the recombination velocity at the interface.

In some cases, for the DTI interfaces, the distant between interfaces $d_{interfaces}$ can be approximately 1 µm (i.e., for a pixel having a dimension of 1 µm). The interfacial recombination rate for a well-passivated interface is in the range of 1 to 10 cm/sec. Assuming an interfacial recombination rate of 10 cm/sec, one can expect that the DTI interfacial recombination life time $t_{recombination,DTI}$ to be about $5\times10^{-6}$ sec. This will control the effective life time $t_{life,effective}$ in a pixel if there are no bulk defects and the surfaces are well passivated.

The effective life time $t_{life,effective}$ depends on the injection level (e.g., the intensity of light incident on the CIS active area). Thus, the effective life time $t_{life,effective}$ can be controlled, at least in part, by adjusting the injection level (e.g., by adjusting the intensity of the excitation light illuminating the CIS sample). The injection level can be adjusted according to one or more criteria.

For example, in some cases, the injection level can be adjusted in order to reduce Auger recombination contribution to the effective life time in the CIS active area. At high injection levels, the effective life time can be controlled by Auger recombination. For example, in some cases, for a $1\times10^{17}$ cm$^{-3}$ injection level, the Auger recombination limits the effective life time in p-type silicon to $1\times10^{-4}$ seconds. As another example, in some cases, for a $1\times10^{18}$ cm$^{-3}$ injection level, the Auger recombination limits the effective life time in p-type silicon to $1\times10^{-6}$ seconds. Since Auger recombination is not sensitive to defects, the injection level can be adjusted such that Auger recombination in the CIS active area does not dominate the recombination processes.

Further, Auger recombination also controls the effective life time in the highly doped substrate. For instance, for p++ and n++ substrates, Auger recombination can limit the effective life time for all injection levels. As an example, in some cases, in a p++ substrate having a $1\times10^{20}$ cm$^{-3}$ carrier concentration, the effective life time is limited to $1\times10^{-9}$ sec. The Auger recombination life time changes abruptly with dopant concentration. For example, a ten times reduction of the dopant concentration (e.g., from a dopant concentration of $1\times10^{20}$ to $1\times10^{19}$) will increase the effective life time one hundred times (e.g., to $1\times10^{-7}$ sec).

The effective life time in the CIS active area also depends on the injection level at a low injection level regime (e.g., when the contribution of Auger recombination is negligible). Thus, it is important to monitor photoluminescence intensity as a function of the illumination level (i.e., injection level), since the life time response to the injection level could be different for various defects. For example, given a p-type silicon, a defect such as interstitial Fe will result in an increase in the effective life time as the injection level is increased. However, a defect such as a Fe—B pair will result in a decrease in the effective life time with an increase of injection level. For a defect which increases recombination at the interface (e.g., $SiO_2$ interfaces or walls of the DTI), the effect of the changing injection level on the interfacial recombination life time will depend on a state of a space charge region at this interface. For the interface in an inversion at low injection levels, the interface recombination lifetime does not change with an increasing injection level. When the injection level becomes high (e.g., larger than the majority carrier concentration), then the life time decreases with the increasing injection level. For the interface in a depletion for the low injection levels, the interfacial recombination life time increases with the increasing injection level. But, for high injection levels, the interfacial recombination life time does not change with an increase in injection level. Therefore, for a given defective pixel, the dependence of the photoluminescence intensity on the injection level could provide an important clue to a nature of this defect.

As discussed above, in some cases, it is important to contain photoluminescence to the CIS active area and use appropriately low injection levels. Further, it is important to minimize or otherwise appropriate reduce the amount of light that is absorbed in the highly doped substrates. Photoluminescence intensity is proportional to the majority carrier concentration. Thus, for the same amount of photons absorbed in the substrate and the epitaxial layer (e.g., the CIS active area), photoluminescence from the substrate could be stronger than from the CIS active region. For instance, in an example CIS device, the CIS active region has an average dopant concentration of $1\times10^{16}$ cm$^{-3}$ at the beginning of processing, and has an effective life time of $5\times10^{-6}$ sec. The substrate in this example has an average dopant concentration of $1\times10^{19}$ cm$^{-3}$, and has an effective life time of $1\times10^{-7}$ (controlled by the Auger recombination) which, in some cases, can result in a diffusion length (e.g., the distance that minority carriers will diffuse) of approximately 20 µm. Given similar amounts of absorbed photons in the CIS active region and the highly doped substrate, the photoluminescence from the substrate will be five times more intense than for the CIS active area. To minimize the background photoluminescence from the substrate to less than 5% of the photoluminescence from the CIS active area, the amount of photons absorbed in the substrate can be limited to less than 1% of the photons absorbed in the CIS active area. Therefore, the wavelength of the photoluminescence generating light (e.g., absorption coefficient) can be chosen appropriately.

As described above, in some cases, it is also important to induce photoluminescence using an injection level at which the Auger recombination does not control the life time in the active area of the CIS sample (e.g., when the contribution of Auger recombination in the CIS active area is negligible). As discussed above, for an injection level of $1\times10^{17}$ cm$^{-3}$, the Auger life time is $1\times10^{-4}$ sec. But, for an injection level of $1\times10^{18}$ cm$^{-3}$, the Auger life time is $1\times10^{-6}$. As an example, in some cases, for an CIS active area with an effective (i.e., bulk and interfacial recombination) life time in the range of $5\times10^{-6}$, the injection level of $1\times10^{18}$ cm$^{-3}$ can be avoided, as the sensitivity to the bulk and the interfacial recombination would be lost at this injection level, and will contribute less than 20% to the measured effective lifetime.

In some cases, it is also important to induce photoluminescence using an injection level that will prevent out diffusion of minority carriers from the CIS active area to the highly doped substrate. An important concern regarding the injection level (e.g., the minority carrier concentration generated in the CIS active region) is related to out diffusion of minority carriers generated in the CIS active area into the highly doped substrate. Due to the dopant concentration difference between the highly doped p++ substrate and the lighter doped p-type materials in the CIS active area, an electric field exists at the p/p++ interface which, for low injection levels, will impede diffusion of the minority carriers from the CIS active area into the substrate. However, the difference in the minority carrier concentrations in the CIS active region and the substrate will generate a diffusion field which will be the driving force for the minority carrier diffusion from the CIS active region into the substrate. As the injection level increases, this diffusion driving force will also increase. As long as the diffusion force is smaller than the electric repulsion, the minority carriers will be contained in the epitaxial layer. For high injection levels, this diffusion gradient can overcome the electric repulsion and some minority carriers could enter into the substrate. As a result, a strong background photoluminescence will be generated from the substrate. This will reduce the sensitivity of detecting photoluminescence changes from the CIS active area.

Therefore, in order to enhance the detection sensitivity of the system 100 and to minimize photoluminescence generation in the highly doped substrate of a CIS sample, it is important to select an appropriate wavelength and intensity for the excitation light that is applied to the CIS sample.

In some cases, the wavelength and intensity of the excitation light can evaluated empirically for each application. For example, the empirical determination can be made regarding whether the wavelength and intensity of the excitation light results in photoluminescence that is predominantly from the active area of the CIS sample, or whether the resulting photoluminescence has a large contribution from the substrate of the CIS sample.

In an example evaluation process, the CIS sample is illuminated with excitation light having a particular wavelength and intensity, and the resulting photoluminescence is detected over a relatively large portion of the CIS sample (e.g., a "macro" region). In some cases, the portion of the CIS sample that is examined in this manner can be larger than the portions of the CIS sample measured by the detectors 172a-b, as described above. In some cases, this "macro" region can have an area of approximately 1 cm$^2$ or larger (e.g., 1 cm$^2$, 2 cm$^2$, 3 cm$^2$, 4 cm$^2$ or larger). In some cases, this "macro" region can include the entire CIS sample.

In some cases, the photoluminescence of this "macro" region can be determined using a detector that is separate from the detectors 172a-b. For example, a separate detector can be directed towards the CIS sample 190 in order to acquire photoluminescence measurements of the "macro" region alongside the detectors 172a-b. In some cases, the photoluminescence of this "macro" region can be determined by one of the detectors 172a-b. For example, in some implementation, the optical path between the CIS sample 190 and the detectors 172a-b can be varied while imaging the "macro" region, such as by using a different objective lens 154 or adjusting the optical properties of the objective lens 154 while imaging the "macro" region.

Figure 2:
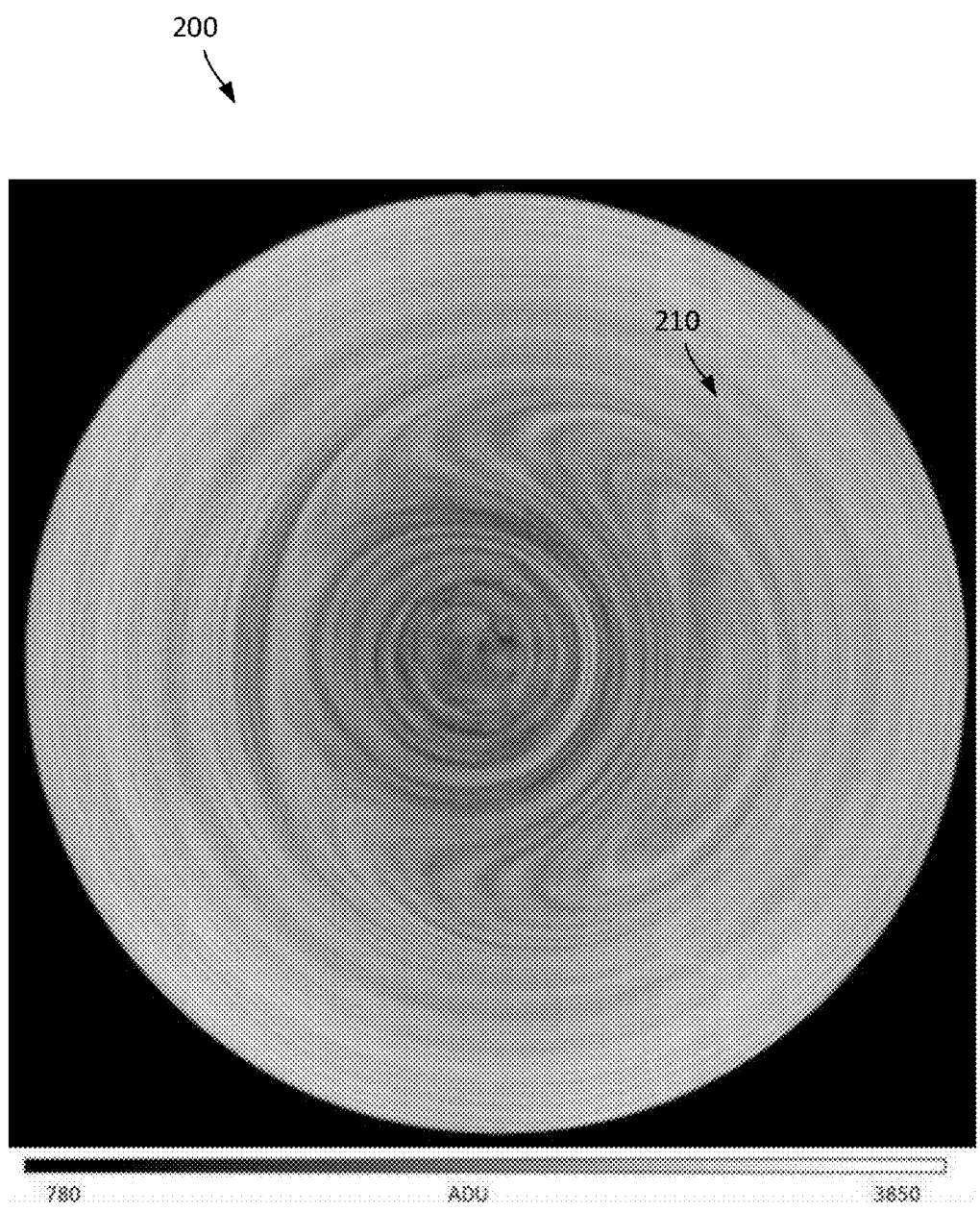
FIG. 2 shows a photoluminescence intensity map having variations in photoluminescence intensity characteristic of defects in a silicon substrate.

The resulting photoluminescence map is examined for variations in intensity indicative of defects typically associated with the silicon substrate of a CIS device. For instance, silicon wafers manufactured by the Czochralski process (i.e., "CZ wafers") often include curved variations in photoluminescence when illuminated by excitation light. As an example, FIG. 2 shows an example photoluminescence map 200 for a CIS device. In this example, the photoluminescence map 200 includes several variations in photoluminescence intensity 210, appearing as circular or curved bands of intensity variation. In some cases, variations similar to those shown in FIG. 2 are characteristic of silicon wafers manufactured by the Czochralski process, and this characteristic pattern is not present in the epitaxial layers of the device (e.g., CIS active area).

The contribution of photoluminescence from the substrate to the total detected photoluminescence can be quantitatively calculated by illuminating the CIS sample with long wavelength illumination (e.g., near infrared illumination with an energy large than approximately 1.1 eV, the energy gap of Si), such that a large portion of the carriers (e.g., substantially most or substantially all of the carriers) are generated in the substrate. The changes in this photoluminescence intensity due to the characteristic substrate defects are used as a reference for calculations in the substrate photoluminescence contribution to the total photoluminescence detected for the short wavelength.

As an example, when the CIS sample is illuminated with excitation light having a relatively long wavelength (e.g., excitation light having a wavelength that causes substantially most or substantially all of the carriers to be generated in the substrate of the CIS sample), the defect contrast is 50% (e.g., the photoluminescence intensity map includes localized variations in intensity of that differ the surrounding intensity by 50%). However, when the CIS sample is illuminated with excitation light having a relatively shorter wavelength, the defect contrast is 5% (e.g., the photoluminescence intensity map includes localized variations in intensity of that differ the surrounding intensity by 5%). Thus, in this example, one can estimate that the substrate contribution to the total photoluminescence for the relatively shorter wavelength is about 10% (e.g., 5% divided by 50%).

If the substrate contribution to photoluminescence is too large, then the measurement conditions can be adjusted (e.g., by reducing the wavelength or light intensity to the excitation light applied to the CIS sample) until the defect pattern is reduced or eliminated.

In some cases, the upper injection limit that can be used for the detection of defects in a CIS sample can be determined, at least in part, based on the Auger recombination life time, which decreases with increasing injection level. As an example, for an injection level of $1 \times 10^{17}$ cm$^{-3}$, the Auger life time in an example device is $100 \times 10^{-6}$ sec. For a CIS active region with a $5 \times 10^{-6}$ sec effective recombination life time from bulk and interfacial recombination, this Auger recombination will contribute about 5% to the effective life time.

The sensitivity of the system 100 to defects in the CIS sample depends, at least in part, on the bulk and interfacial recombination lifetime being shorter than the Auger recombination life time. In some cases, the wavelength and intensity of the excitation light can be varied in order to obtain a particular percentage of contribution Auger recombination to the effective life time. For example, in some implementations, the wavelength and intensity of the excitation light can be varied such that the Auger life time of the CIS active region is less than or equal to 5% of the effective recombination life time from bulk and interfacial recombination of the CIS active region. In some implementation, this threshold corresponds to an injection level of approximately $1 \times 10^{17}$ cm$^{-3}$ or less. For the CIS active area of approximately 5 μm thickness, in some cases, this will correspond to the absorption of about $1 \times 10^{19}$ photons/cm$^2$ sec (e.g., corresponding to a power of 100 mW/cm$^2$) in the CIS active region. Although an example threshold is described above, this is merely an illustrative example. In some cases, the wavelength and intensity of the excitation light can be varied such that the Auger life time of the CIS active region is less than or equal to some other percentage of the effective recombination life time from bulk and interfacial recombination of the CIS active region (e.g., 1%, 5%, 10%, 15%, or any other percentage).

Although implementations for detecting defects in CIS devices are described herein, this is merely one illustrative application. In practice, implementations can be used to detect defects in other devices or circuit in which generated minority carriers and photoluminescence are substantially confined to device active region. For example, in some cases, implementations can be used to detect defects in CMOS circuits built using fully depleted silicon on insulator (SOI) technologies.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of implementations have been described. Nevertheless, it will be understood that various modifications may be made without departing from the spirit and scope of the invention. Accordingly, other implementations are within the scope of the following claims.

What is claimed is:

1. A method comprising:
    continuously illuminating a portion of a wafer with excitation light having a wavelength and intensity sufficient to induce photoluminescence in the portion of the wafer and having an intensity sufficiently low such that Auger recombination does not substantially occur in the portion of the wafer;
    detecting photoluminescence emitted from a portion of the wafer in response to the illumination, the detecting comprising integrating a detected intensity over a period during which the wafer is continuously illuminated;
    detecting excitation light reflected from the same portion of the wafer;
    comparing the detected photoluminescence from the portion of the wafer and the detected excitation light reflected from the same portion of the wafer; and
    identifying one or more defects in the wafer based on the comparison.

2. The method of claim 1, wherein the wafer comprises a complementary metal-oxide semiconductor (CMOS) imaging sensor.

3. The method of claim 2, wherein the portion of the wafer comprises one or more pixels of the CMOS imaging sensor.

4. The method of claim 3, wherein identifying one or more defects in the wafer comprises identifying one or more defective pixels of the CMOS imaging sensor.

5. The method of claim 3, wherein detecting photoluminescence emitted from the portion of the wafer comprises resolving photoluminescence emitted from the portion of the wafer at a spatial resolution of 1 µm×1 µm or smaller.

6. The method of claim 3, wherein detecting excitation light reflected from the same portion of the wafer comprises resolving excitation light reflected from the same portion of the wafer at a spatial resolution of 1 µm×1 µm or smaller.

7. The method of claim 3, wherein identifying one or more defects in the wafer comprises identifying one or more defects having a dimension of 1 µm or smaller.

8. The method of claim 2, wherein the portion of the wafer corresponds to an active area of the CMOS imaging sensor.

9. The method of claim 1, further comprising:
    forming a photoluminescence intensity map of the portion of the wafer based on the photoluminescence emitted from the portion of the wafer; and
    forming a reflection intensity map of the portion of the wafer based on the excitation light reflected from the same portion of the wafer.

10. The method of claim 9, wherein comparing the detected photoluminescence from the portion of the wafer and the detected reflected excitation light from the same portion of the wafer comprises:
    determining that the photoluminescence intensity map includes a first variation in intensity at a first location of the wafer;
    upon determining that the photoluminescence intensity map includes the first variation in intensity at the first location of the wafer, determining whether the reflection intensity map includes a second variation in intensity at the first location of the wafer;
    upon determining that the reflection intensity map does not include a second variation in intensity at the first location of the wafer, determining that a defect is present at the first location of the wafer.

11. The method of claim 10, wherein comparing the detected photoluminescence from the portion of the wafer and the detected reflected excitation light from the same portion of the wafer further comprises:
    upon determining that the reflection intensity map includes the second variation in intensity at the first location of the wafer, determining that a defect is not present at the first location of the wafer.

12. The method of claim 1, wherein the excitation light has a wavelength in a range from 200 nm to 1,100 nm.

13. The method of claim 1, wherein the photoluminescence has as a wavelength in a range from 200 nm to 1,100 nm.

14. The method of claim 1, wherein the photoluminescence emitted from the portion of the wafer and the excitation light reflected from the same portion of the wafer are detected with respect to an entire region simultaneously illuminated with excitation light.

15. The method of claim 1, wherein the portion of the wafer has an area of approximately 1 cm$^2$ or larger.

16. The method of claim 15, wherein the portion of the wafer is an entirety of the wafer.

17. The method of claim 1, wherein detecting photoluminescence emitted from the portion of the wafer comprises sequentially detecting photoluminescence emitted from multiple different depths below a surface of the wafer.

18. The method of claim 1, wherein detecting photoluminescence emitted from the portion of the wafer comprises:
    detecting first photoluminescence emitted from a first depth below a surface of the wafer, and
    separately from detecting the first photoluminescence, detecting second photoluminescence emitted from a second depth below the surface of the wafer, wherein the first depth is different than the second depth.

19. The method of claim 1, where illuminating the wafer with excitation light comprises directing excitation light onto a surface of the wafer via an objective lens, and
    wherein detecting photoluminescence emitted from the portion of the wafer comprises receiving photoluminescence emitted from the portion of the wafer via the objective lens.

20. The method of claim 1, wherein the photoluminescence emitted from the portion of the wafer and the excitation light reflected from the same portion of the wafer are detected simultaneously.

21. The method of claim 1, wherein the detected excitation light is reflected from the same portion of the wafer.

22. A method comprising:
    illuminating a wafer with excitation light having a wavelength and intensity sufficient to induce photoluminescence in the wafer;
    detecting photoluminescence emitted from a portion of the wafer in response to the illumination;

detecting excitation light reflected from the same portion of the wafer;
comparing the detected photoluminescence from the portion of the wafer and the detected excitation light reflected from the same portion of the wafer;
identifying one or more defects in the wafer based on the comparison;
detecting photoluminescence emitted from a second portion of the wafer, wherein the second portion of the wafer is larger than the first portion of the wafer;
forming a photoluminescence intensity map of the second portion of the wafer based on the photoluminescence emitted from the second portion of the wafer;
determining the presence of one or more curved regions of contrast in the photoluminescence intensity map; and
upon determining the presence of one or more curved regions of contrast in the photoluminescence intensity map, adjusting a property of the excitation light.

23. The method of claim 22, wherein the one or more curved regions of contrast are indicative of defects in silicon wafers manufactured by the Czochralski process.

24. The method of claim 22, wherein adjusting the property of the excitation light comprises adjusting a wavelength of the excitation light to increase the photoluminescence emitted from the second portion of the wafer.

25. The method of claim 22, wherein adjusting the property of the excitation light comprises adjusting an intensity of the excitation light.

26. A system comprising:
one or more light sources configured to continuously illuminate a portion of a wafer with excitation light having a wavelength and intensity sufficient to induce photoluminescence in the portion of the wafer and having an intensity sufficiently low such that Auger recombination does not substantially occur in the portion of the wafer;
a first detector configured to detect photoluminescence emitted from a portion of the wafer in response to the illumination over a period during which the wafer is continuously illuminated, the detector integrating the detected intensity over the period;
a second detector configured to detect excitation light reflected from the same portion of the wafer; and
one or more processors configured to:
compare the detected photoluminescence from the portion of the wafer and the detected excitation light reflected from the same portion of the wafer; and
identify one or more defects in the wafer based on the comparison.

27. The system of claim 26, wherein the wafer comprises a complementary metal-oxide semiconductor (CMOS) imaging sensor.

28. The system of claim 27, wherein the portion of the wafer comprises one or more pixels of the CMOS imaging sensor.

29. The system of claim 28, wherein identifying one or more defects in the wafer comprises identifying one or more defective pixels of the CMOS imaging sensor.

30. The system of claim 29, wherein detecting photoluminescence emitted from the portion of the wafer comprises resolving photoluminescence emitted from the portion of the wafer at a spatial resolution of 1 µm×1 µm or smaller.

31. The system of claim 29, wherein detecting excitation light reflected from the same portion of the wafer comprises resolving excitation light reflected from the same portion of the wafer at a spatial resolution of 1 µm×1 µm or smaller.

32. The system of claim 29, wherein identifying one or more defects in the wafer comprises identifying one or more defects having a dimension of 1 µm or smaller.

33. The system of claim 27, wherein the portion of the wafer corresponds to an active area of the CMOS imaging sensor.

34. The system of claim 26, wherein the one or more processors are further configured to:
form a photoluminescence intensity map of the portion of the wafer based on the photoluminescence emitted from the portion of the wafer; and
form a reflection intensity map of the portion of the wafer based on the excitation light reflected from the same portion of the wafer.

35. The system of claim 26, wherein comparing the detected photoluminescence from the portion of the wafer and the detected reflected excitation light from the same portion of the wafer comprises:
determining that the photoluminescence intensity map includes a first variation in intensity at a first location of the wafer;
upon determining that the photoluminescence intensity map includes the first variation in intensity at the first location of the wafer, determining whether the reflection intensity map includes a second variation in intensity at the first location of the wafer;
upon determining that the reflection intensity map does not include a second variation in intensity at the first location of the wafer, determining that a defect is present at the first location of the wafer.

36. The system of claim 35, wherein comparing the detected photoluminescence from the portion of the wafer and the detected reflected excitation light from the same portion of the wafer further comprises:
upon determining that the reflection intensity map includes the second variation in intensity at the first location of the wafer, determining that a defect is not present at the first location of the wafer.

37. The system of claim 26, wherein the excitation light has a wavelength in a range from 200 nm to 1,100 nm.

38. The system of claim 26, wherein the photoluminescence has as a wavelength in a range from 200 nm to 1,100 nm.

39. The system of claim 26, wherein the second detector is configured to detect excitation light reflected from the same portion of the wafer.

40. A system comprising:
one or more light sources configured to illuminate a wafer with excitation light having a wavelength and intensity sufficient to induce photoluminescence in the wafer;
a first detector configured to detect photoluminescence emitted from a portion of the wafer in response to the illumination;
a second detector configured to detect excitation light reflected from the same portion of the wafer;
a third detector configured to detect photoluminescence emitted from a second portion of the wafer, wherein the second portion of the wafer is larger than the first portion of the wafer; and
one or more processors configured to:
compare the detected photoluminescence from the portion of the wafer and the detected excitation light reflected from the same portion of the wafer;
identify one or more defects in the wafer based on the comparison;

form a photoluminescence intensity map of the second portion of the wafer based on the photoluminescence emitted from the second portion of the wafer;

determine the presence of one or more curved regions of contrast in the photoluminescence intensity map; and upon determining the presence of one or more curved regions of contrast in the photoluminescence intensity map, adjust a property of the excitation light.

41. The system of claim 40, wherein the one or more curved regions of contrast are indicative of defects in silicon wafers manufactured by the Czochralski process.

42. The system of claim 40, wherein adjusting the property of the excitation light comprises adjusting a wavelength of the excitation light to increase the photoluminescence emitted from the second portion of the wafer.

43. The system of claim 40, wherein adjusting the property of the excitation light comprises adjusting an intensity of the excitation light.

* * * * *

UNITED STATES PATENT AND TRADEMARK OFFICE
CERTIFICATE OF CORRECTION

PATENT NO. : 10,012,593 B2
APPLICATION NO. : 14/703692
DATED : July 3, 2018
INVENTOR(S) : Zoltan Tamas Kiss et al.

It is certified that error appears in the above-identified patent and that said Letters Patent is hereby corrected as shown below:

In the Claims

In Column 18, Line 61, In Claim 21, after "is" insert -- specularly --.

In Column 20, Line 47, In Claim 39, after "light" insert -- specularly --.

In Column 20, Line 64, In Claim 39, after "light" insert -- specularly --.

Signed and Sealed this
Fourth Day of June, 2019

Andrei Iancu
*Director of the United States Patent and Trademark Office*